(12) United States Patent
Melikechi

(10) Patent No.: US 10,309,880 B2
(45) Date of Patent: Jun. 4, 2019

(54) PREPARATION OF FLUID SAMPLES FOR LASER INDUCED BREAKDOWN SPECTROSCOPY AND/OR IMAGING ANALYSIS

(71) Applicant: DOVER PHOTONICS LLC, Newark, DE (US)

(72) Inventor: Noureddine Melikechi, Dover, DE (US)

(73) Assignee: Dover Photonics LLC, Newark, DE (US)

( * ) Notice: Subject to any disclaimer, the term of this patent is extended or adjusted under 35 U.S.C. 154(b) by 3 days.

(21) Appl. No.: 15/561,836

(22) PCT Filed: Mar. 25, 2016

(86) PCT No.: PCT/US2016/024150
§ 371 (c)(1),
(2) Date: Sep. 26, 2017

(87) PCT Pub. No.: WO2016/154509
PCT Pub. Date: Sep. 29, 2016

(65) Prior Publication Data
US 2018/0120205 A1    May 3, 2018

Related U.S. Application Data

(60) Provisional application No. 62/138,676, filed on Mar. 26, 2015.

(51) Int. Cl.
*G01N 1/38* (2006.01)
*G01N 1/40* (2006.01)
(Continued)

(52) U.S. Cl.
CPC .............. *G01N 1/4077* (2013.01); *G01N 1/38* (2013.01); *G01N 21/01* (2013.01); *G01N 21/63* (2013.01);
(Continued)

(58) Field of Classification Search
CPC ........ G01N 1/4077; G01N 1/38; G01N 21/01; G01N 21/63; G01N 21/718;
(Continued)

(56) References Cited

U.S. PATENT DOCUMENTS 5,149,496 A    9/1992  Das
5,545,360 A    8/1996  Yang
(Continued)

FOREIGN PATENT DOCUMENTS

WO    2006135384 A1    12/2006
WO    2007004167 A1    1/2007

OTHER PUBLICATIONS

Jantzi et al., "Sample treatment and Preparation for Laser-induced Breakdown Spectroscopy", Spectrochimica Acta Part B Atomic Spectroscopy, Nov. 2015, pp. 52-63.
(Continued)

*Primary Examiner* — Dominic J Bologna
(74) *Attorney, Agent, or Firm* — RatnerPrestia

(57) ABSTRACT

A method of analyzing, preferably by laser induced breakdown spectroscopy (LIBS), fluid samples (e.g. liquids, solutions, melts or slurries) that contain soluble and insoluble components of various elemental, molecular and biological components using a pre-characterized, preferably non-magnetic, membrane or plurality of membranes each having different characteristics, such as different porosities. The fluid sample is first deposited on the one or more membranes and the components to be analyzed are retained thereon through filtration or diffusion and then analyzed, such as
(Continued)

with LIBS. Different components, such as different sized particles, are fixed on different membranes depending on the characteristics (e.g. pore size) of the corresponding membrane, which provides pre-sorting of the components before LIBS analysis.

31 Claims, 2 Drawing Sheets

(51) Int. Cl.
    *G01N 21/01*     (2006.01)
    *G01N 21/63*     (2006.01)
    *G01N 21/71*     (2006.01)

(52) U.S. Cl.
    CPC ..... *G01N 21/718* (2013.01); *G01N 2001/381* (2013.01); *G01N 2001/4038* (2013.01); *G01N 2001/4088* (2013.01)

(58) Field of Classification Search
    CPC ..... G01N 2001/381; G01N 2001/4038; G01N 2001/4088
    See application file for complete search history.

(56) References Cited

U.S. PATENT DOCUMENTS

| | | | |
|---|---|---|---|
| 5,628,945 | A | 5/1997 | Riman |
| 6,232,372 | B1 | 5/2001 | Brothers et al. |
| 6,342,396 | B1 | 1/2002 | Perrin et al. |
| 7,341,757 | B2 | 3/2008 | Yadaov |
| 7,367,999 | B2 | 5/2008 | Fujimoto |
| 7,368,130 | B2 | 5/2008 | Kim et al. |
| 7,381,467 | B2 | 6/2008 | Arai et al. |
| 7,384,798 | B2 | 6/2008 | Harding et al. |
| 2004/0072250 | A1 | 4/2004 | Baranov |
| 2005/0037397 | A1 | 2/2005 | Mirkin et al. |
| 2007/0046934 | A1 | 3/2007 | Roy |
| 2008/0090737 | A1 | 4/2008 | Boschetti |
| 2011/0171636 | A1 | 7/2011 | Melikechi et al. |
| 2011/0246145 | A1* | 10/2011 | Multari ............ G01J 3/28 703/2 |
| 2014/0368819 | A1* | 12/2014 | Multari ............ A61B 5/4845 356/318 |
| 2017/0322162 | A1* | 11/2017 | Park ............ G01N 1/44 |

OTHER PUBLICATIONS

Kim at al., "Laser-induced Breakdown Spectroscopy", InTech, 2012, pp. 153-159.
International Preliminary Report on Patentablity for International Application No. PCT/US2016/024150, dated Sep. 26, 2017—6 Pages.
International Search Report and Written Opinion for International Application No. PCT/US2016/024150, dated Aug. 11, 2016—6 Pages.
Polyakov E. V. et al.; Sovremennye metody opredeleniya fiziko-himicheskogo sostoyaniya mikroelementov v prirodnyh vodah. pp. 1103-1114. Nov. 2, 2002. with English abstract included, English title is "Modern Methods for the Determination of Physicochemical States of Microelements in Natural Waters."
Song, K. et al., "Applications of laser-induced breakdown spectrometry" , Appl. Spectros. Rev. 32, 183-235 (1997).
Arca, G. et al., "Trace element analysis in water by laser-induced breakdown Spectroscopy" , Appl. Spectros. 51, 1102-1105 (1997).
Kumar, A. et al., "Characterization of malignant tissue cells by laser-induced breakdown spectroscopy" , Appl. Opt. 43, 5399-5403 (2004).
Samuels, A. C. et al., "Laser-induced breakdown spectroscopy of bacterial spores, molds, pollens, and protein: initial studies of discrimination potential" , Appl. Opt. 42, 6205-6209 (2003).
Boyain-Goitia, A. R. et al., "Single-pollen analysis by laser-induced breakdown spectroscopy and Raman microscopy" , Appl. Opt. 42, 6119-6132 (2003).
Morel, S. et al., "Detection of bacteria by time-resolved laser-induced breakdown spectroscopy" , Appl. Opt. 42, 6184-6191, (2003).
Gretzer, M. B. et al., "Modern tumor marker discovery in urology: Surface Enhanced Laser Desorption and Ionization (SELDI)" , Rev. Urol. 5, 81-89 (2003).
Hybl, J. et al, "Laser-induced break-down spectroscopy detection and classification of biological aerosols" , Appl. Spectros 57, 1207-1215 (2003).
Vashist, S.K.. et al., "Review of Quantum Dot Technologies for Cancer Detection and Treatment", The AZo Journal of Nanotechnology Online, vol. 2, Sep. 2006, pp. 1-14, azonano.com/Details.asp?ArticleID=1726.
Expand your horizons in flow cytometry with Qdot nanocrystals, Invitrogen Corporation brochure, tools.invitrogen.com/content/sfs/brochures/F074015Qdot_primaries_pp.pdf).
Carranza, J. E. et al., "Conditional data processing for single-shot spectral analysis by use of laser-induced breakdown spectroscopy" , Appl. Opt. 42, 6022-6028, (2003).
Jovin T. M., "Quantum dots finally come of age" , Nature Biotechnology 21, 32-33,(2003).
Thermo Scientific Pierce Crosslinking Technical Handbook, pp. 1-45, piercenet.com/files/1601361 Crosslink.pdf.
piercenet.com/files/2066as4.pdf, pp. 1-4.
Khire, V.S. et al., "Surface Modification Using Thiol-Acrylate Conjugate Addition Reactions" , Macromolecules, 40 (16), 5669-5677, 2007.
Rock, S. et al., "Elemental analysis of laser induced breakdown spectroscopy aided by an empirical spectral database", Applied Optics. 47, pp. G99-G104 (2008).
Melikechi, N. et al., "Laser-induced breakdown spectroscopy of alcohols and proteins solutions", AIP Proceedings: Atomic, Molecular, and Optical Physics 992, 1177-1182 (2008).
Melikechi, N. et al., "Laser-induced breakdown spectroscopy of whole blood and other liquid organic compounds" Optical Diagnostic and Sensing VIII, Editors G. Cote and A. Priezzhev, Proc. of SPIE 6863, 68630O (2008), DOI:10.1117/12.761901.
Markushin, Y. et al., "Determination of protein hydrogen composition by laser-induced breakdown spectroscopy", J. Anal. At. Spectrom. 25, 148-149 (2010).
Han M. et al., "Quantum-dot-tagged microbeads for multiplexed optical coding of biomolecules" , Nature Biotechnol. 19 (7), 631-635 (2001).
Markushin, et al., "LIBS-based multi-element coded assay for ovarian cancer application," Proc. of SPIE 7190: 719015-1-79015-6, 2009.
Harma, H., "Particle technologies in diagnostics, www.tekesli/julkaisut/particle.pdf ", Finland National Technology Agency, Technology Review 126, (2002).
Yueh, F-Y., et al., "Laser-induced Breakdown Spectroscopy, Elemental Analysis", Encyclopedia of Analytical Chemistry, R.A. Meyers (Ed.), John Wiley & Sons Ltd, Chichester, 2066-2087 (2000).
Yamamoto, K.Y., et al., "Detection of Metals in the Environment Using a portable Laser-induced Breakdown Spectroscopy Instrument", Appl. Spectrosc. 50, 222-233 (1996).
Doig A. R., "Molecular Diagnostics Market Assessment, Technological Innovation Continues to Refine these Effective Tools for Disease Management" , Genetic Engineering & Biotechnology News, Feb. 1, 2007 (vol. 27, No. 3).
Muller et al., Detection of Specific Proteins by Laser Albation Inductively Coupled Plasma Mass Spectrometry (LA-ICP-MS) Using Gold Cluster Labelled Antibodies, Aug. 8, 2005, J. Anal. At. Spectrom., 20, pp. 907-911.

* cited by examiner

PREPARATION OF FLUID SAMPLES FOR LASER INDUCED BREAKDOWN SPECTROSCOPY AND/OR IMAGING ANALYSIS

CROSS REFERENCE TO RELATED APPLICATIONS

This application is a U.S. National Phase Patent Application of International Application No. PCT/US2016/024150 filed Mar. 25, 2016, titled PREPARATION OF FLUID SAMPLES FOR LASER INDUCED BREAKDOWN SPECTROSCOPY AND/OR IMAGING ANALYSIS, which claims priority from U.S. Provisional Patent Application 62/138,676 filed Mar. 26, 2015 titled PREPARATION OF LIQUID SAMPLES FOR LASER INDUCED BREAKDOWN SPECTROSCOPY AND/OR IMAGING ANALYSIS, the full disclosure of each are hereby incorporated by reference.

BACKGROUND OF THE INVENTION

Laser-induced breakdown spectroscopy (LIBS) has been widely investigated in recent decades for different applications ranging from space exploration to biological specimens. In particular, LIBS can be used in methods to identify biomarkers, such as for diseases such as cancer, present in a biological sample, such as a bodily fluid, by reacting the biomarker with a plurality of element-coded particles each comprising a compound, such as a protein, oligonucleotide, polysaccharide, or lipid, that binds to the biomarker, removing unbound element-coded particles from the sample, detecting the element-coded particles in the sample using a laser-induced breakdown spectrometer, and quantifying the element coded particles in the sample, such as pursuant to the methods described in U.S. Published Pat. App. No. US 20110171636, titled "Mono- and multi-element coded libs assays and methods," listing the present inventor as a co-inventor and incorporated herein in its entirety by reference.

The success of LIBS is due to a set of advantages that makes this analytical technique unique such as multi-element analysis, fast response, remote sensing, little to no sample treatment, the attractive cost of the instrumentation, and its ease of use. Although LIBS was born as a field technique, the improvement in instrumental capabilities and knowledge on fundamental aspects of laser-induced plasma spectroscopy has allowed for a large expansion into laboratory applications. As a result, LIBS is now competing with other conventional laboratory techniques, still holding some of the advantages mentioned above, but at the same time the analytical performance (i.e., accuracy, and laser shot-shot reproducibility) could be improved in order to really be competitive with other well-established techniques. As with any ordinary analytical tool, the laboratory setting introduces the possibility of tighter control of LIBS experimental conditions and the use of more sophisticated analysis protocols and sample treatment.

One of the most widely cited advantages of laser-induced breakdown spectroscopy (LIBS) is that it does not require sample preparation, but this may also be the biggest factor holding it back from becoming a mature analytical technique like LA-ICP-MS, ICP-OES, or XRF. In general, LIBS performance may be enhanced using two main approaches: a) improving the plasma emission signal and b) modifying the specimens. Until now the LIBS community has primarily focused its efforts on enhancing the plasma emission, which tends to increase cost by adding components (e.g., additional lasers, high performance detectors) and calls for specific expertise in the fields of plasma physical chemistry and laser technology. This approach may not meet the requirements of scientists and operators who want to use LIBS in the same ways as they would use any other classical analytical tool. The manipulation of specimens to make them more suitable for laser ablation and LIBS is gaining interest for two reasons. First, to decrease the limits of detection (LOD) in already established LIBS applications and second, to expand the capability of LIBS to those applications where heterogeneity and/or matrix effects had limited its use. The operational cost of sample treatment can be weighed against the advantage of applying LIBS analysis instead of another analytical technique, keeping in mind that most conventional analytical techniques inherently require significant manipulation of specimens to achieve good results.

While there are certain specimen types that are prone to yield excellent LIBS results without any sample treatment (mostly homogeneous solids such as metals, glass, and polymers), the possible applications of LIBS have been greatly expanded through the use of sample preparation techniques that have resulted in analytical performance (i.e., limits of detection, accuracy, and repeatability) on par with XRF, ICP-OES, and often ICP-MS.

Many LIBS researchers have developed, adapted, and improved upon sample preparation techniques for various specimen types in order to improve the quality of the analytical data that LIBS can produce in a large number of research domains. See, e.g., Sarah C. Jantzi et al., "Sample treatment and preparation for laser-induced breakdown spectroscopy," *Spectrochimica Acta Part B Atomic Spectroscopy*, November 2015, co-authored by the present inventor, and incorporated herein by reference.

Despite the many techniques developed, there is still a need in the art to develop sample preparation techniques that take into account how laser energy affects material ejection and, in turn, ablation efficiency. In particular, use of LIBS systems to analyze liquids, solutions and slurry samples or mixtures thereof may cause laser induced splashing from the liquid sample, making it hard to obtain accurate qualitative and quantitative analysis of the samples. Accordingly, there is a particular need in the art for improved sample preparations techniques for "liquids" or "fluid samples," which terms as used herein, except when apparent to the contrary, refer without limitation to any samples comprising at least a liquid fraction, and which may or may not also contain soluble or insoluble components therein.

SUMMARY OF THE INVENTION

One aspect of the invention can be broadly characterized as comprising preparing a sample prior to making a LIBS measurement so that the liquid sample to be analyzed is deposited on a well-characterized and defined membrane.

Thus, one aspect of the invention comprises a method of analyzing, preferably by laser induced breakdown spectroscopy (LIBS), a fluid sample containing one or more soluble or insoluble components. The method comprises the steps of: (a) filtering the fluid sample through or diffusing the sample into one or more preferably non-magnetic or weakly magnetic membranes having known characteristics; and (b) analyzing the one or more membranes using LIBS to obtain a LIBS spectrum. The fluid sample may comprise, for example, a liquid, solution, melt or slurry, and the soluble or insoluble components may comprise elemental, molecular or biological components. Each of the one or membranes may have at least one different the other membranes, such characteristics including but not limited to porosity (i.e. pore size), pores shape, or materials of construction. The pore sizes for the membranes may be, for example, between 10 nm and 10 mm in some non-limiting embodiments. The one or more membranes may comprise any material that is not chemically reactive with the liquid sample, including but not limited to, for example, glass, or more preferably, hydrophilic glass, filters.

Step (b) preferably comprises quantifying the atomic elements present in the one or more membranes using LIBS for each membrane, and reporting the LIBS analysis along with information regarding the character of the membranes, thereby providing, for example, LIBS analysis information relating to components of the sample having a particular particle size or range of particle sizes. The sample components present in the one or more membranes may be classified and identified by analyzing the LIBS spectrum using a multi-variate analysis method, such as but not limited to Principal Component Analysis (PCA) as well as any automatic machine learning techniques for feature selection, such as for example: support vector machines, neural networks, adaptive local hyperplane, K-nearest neighbors, soft independent modeling class analysis, partial least square, and others. The above sample preparation technique may also be applicable to types of analysis other than LIBS analysis.

The method may comprise, preferably prior to step (a), characterizing the one or more membranes by acquiring the LIBS spectra for the one or more membranes. This pre-characterization step may be performed well prior to completing the rest of the method steps, such that when steps (a) and (b) are performed, the characterizations have already been performed and documented. Thus, the method may comprising receiving and using pre-characterized membranes with documented characteristics or performing the characterization close in time to the separation step. The analysis of each of the one or more membranes using LIBS preferably takes into account the characteristics of the membranes, such as the size or shape of the pores, to obtain both the elemental composition and the character (i.e. size or shape) of the particles in the sample.

The method may further comprise a dissolution step prior to step (a). The method may also comprise fixing the retained components on the one or more membranes between steps (a) and (b), wherein the fixing step may comprise using (i) air convection to remove moisture, (ii) using a thermo electric cooler or a thermo electric warmer (heater), (iii) fixing the liquid on the membranes using radiation, such as light or heat radiation, or (iv) a combination of (i)-(iii). The fixing step is not limited to the foregoing, however, and may include any step for removing moisture and hydrates from the sample or otherwise fixing the components by solidifying them before analysis.

The method may further comprise, prior to or following step (a), magnetizing the sample to physically separate the sample into a portion containing magnetic particles and a portion containing non-magnetic particles, and using either the portion containing magnetic particles or the portion containing non-magnetic particles as the fluid sample in step (a), or performing the remaining steps of the method on both portions separately.

DETAILED DESCRIPTION OF THE INVENTION

One aspect of the invention comprises a method of analyzing by laser induced breakdown spectroscopy (LIBS) fluid samples, such as liquids, solutions, melts or slurry samples, that contain soluble and insoluble components of various elemental, molecular and biological components using one or more pre-characterized, preferably non-magnetic, membranes. In embodiment using a plurality of membranes, each membrane preferably has a different porosity. The liquid sample is deposited in or on the one or more membranes. Components of the fluid sample to be analyzed are retained on or in the membranes, such as through filtration or diffusion, and then analyzed with laser induced breakdown spectroscopy (LIBS). In fluid samples with particles, different sized particles are captured by different membranes depending on the pore size of the corresponding membrane, which provides pre-sorting of the particles before LIBS analysis. The membranes are preferably non-magnetic because a magnetic membrane introduces the possibility (depending on the nature of the sample) that magnetically active particles in the plasma are affected by the magnetic field of the membrane, which may complicate the analysis. A membrane that is only weakly magnetic (i.e. having a magnetic field sufficiently weak so as not to complicate the LIBS analysis) may also be used.

Figure 1:
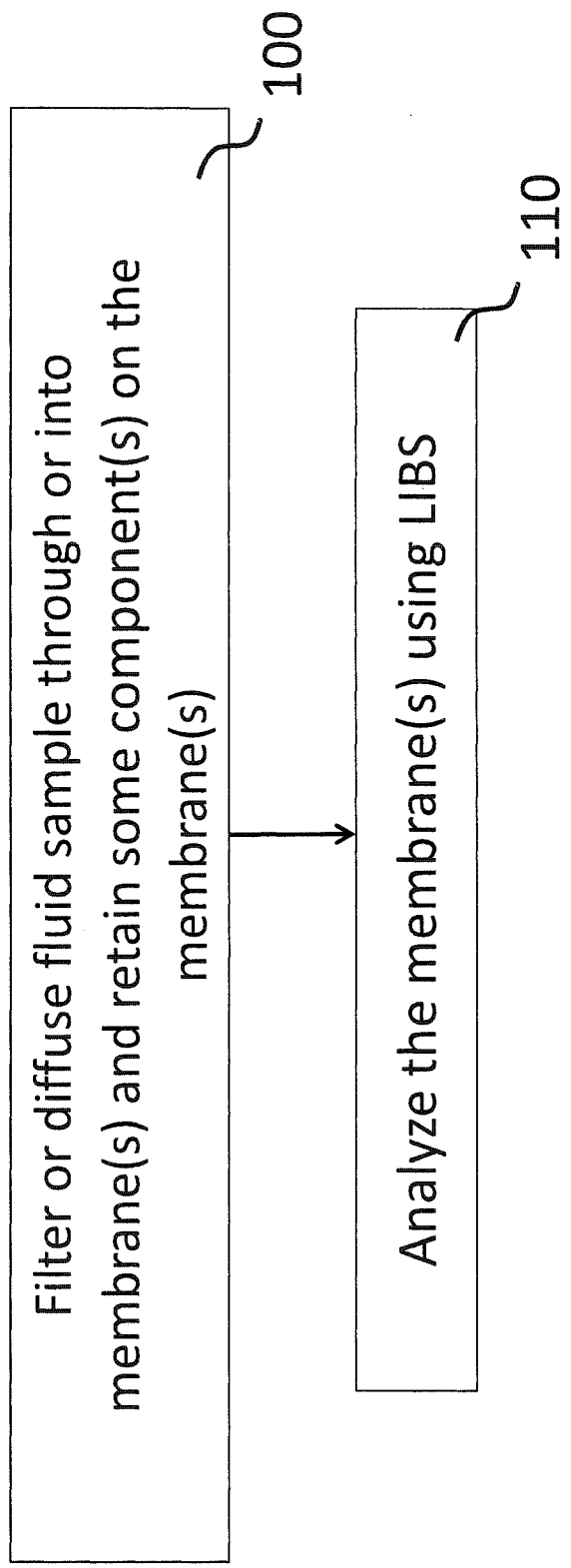
FIG. 1 is a flowchart depicting a basic embodiment of the invention.

Thus, referring to FIG. 1, in its most basic form, one aspect of the invention comprises a method for analyzing a fluid sample comprising step 100 of filtering or diffusing the fluid sample through or into one or more membranes in step such that some components of the fluid sample are retained on or in the one or more membranes, and step 110 of analyzing the one or more membranes using LIBS.

Methods of pre-sorting and preparing the particles before LIBS analysis may comprise (1) an optional electromagnetic separation step, (2) mechanical filtration through one or more porous membranes, and (3) an optional fixation step, such as a drying step, to "fix" the liquid and any components separated by the membranes onto the membranes. The electromagnetic separation may be performed before or after the mechanical filtration step.

Traditionally, LIBS analysis of liquid samples has not been preceded by first preparing the samples. In the embodiments discussed herein, no exterior agents, and specifically no particles, are added to the sample prior to its preparation The samples are processed as set forth herein as is and allowed to diffuse and adsorb to the membranes. In preferred embodiments, the method comprises using a plurality of membranes (including membranes with pores of different sizes, or even in some embodiments, different pore shapes or different materials of construction having different affinities and/or diffusivity coefficients for certain components of the sample). Each membrane having a certain characteristic is then analyzed to produce its own LIBS spectrum. Therefore, each measurement will yield a LIBS spectrum and its corresponding membrane characteristics, and hence an idea of the character (size, shape, etc.) of the particles in the liquid sample, providing richer information regarding the analyzed sample than methods previously known in the art.

An exemplary process of depositing the sample may include leaving the liquid and any retained components on the membrane to dry (causing it to lose water vapor and hydrates) and then analyzing it. The drying process can be performed by various means: (i) air convection to remove moisture, (ii) use of a thermo electric cooler or heater, (iii) use of radiation, such as irradiation with incoherent light of very low power or thermal radiation (heat), and (iv) any combination of the above.

Figure 2:
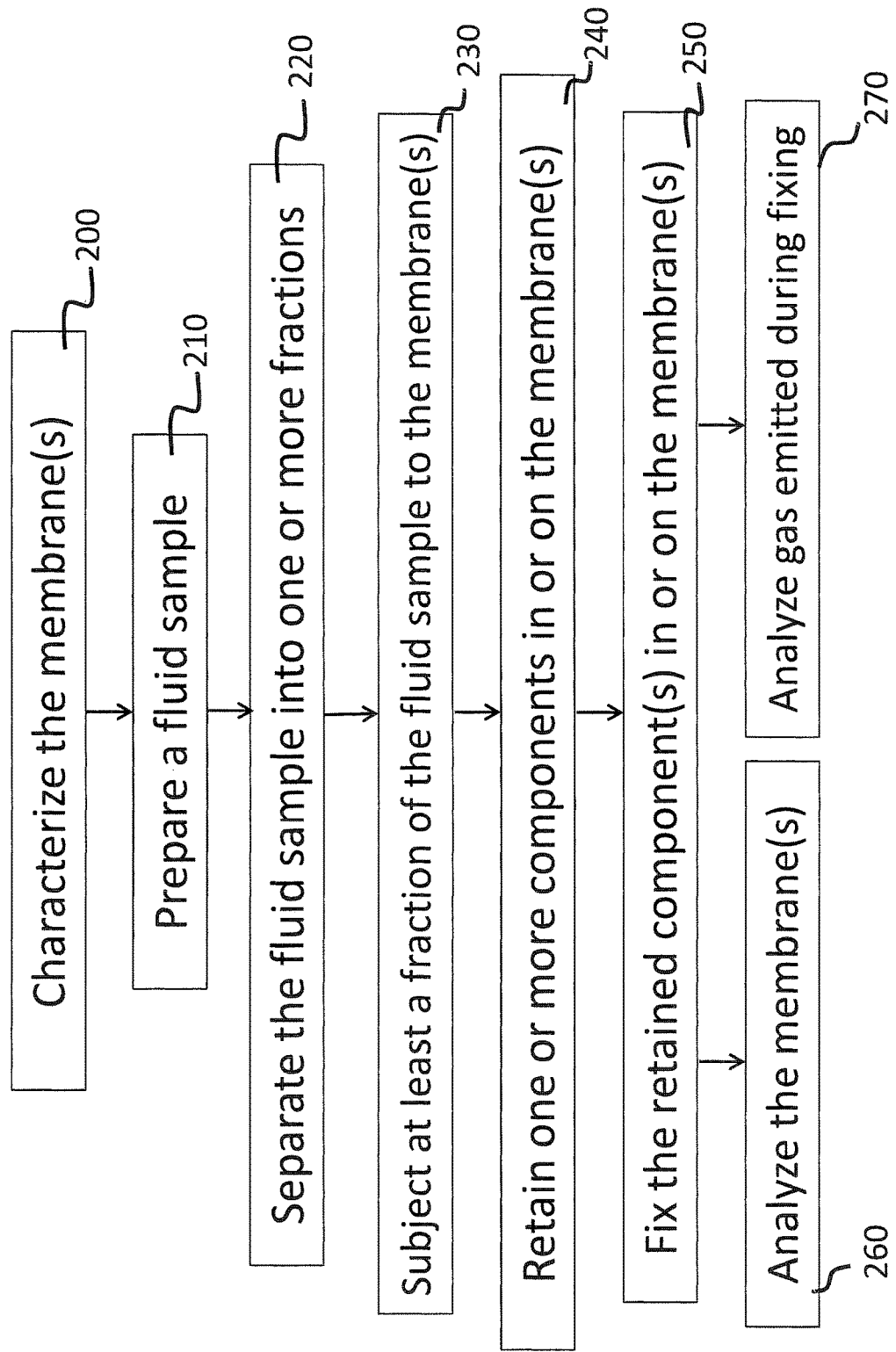
FIG. 2 is a flowchart depicting a detailed embodiment of the invention, including one or more optional steps.

Thus, referring now to FIG. 2, another embodiment of the invention may include first characterizing the one or more membranes in step 200. This step may be performed well in advance of the other steps shown in FIG. 2, and may be performed by a supplier of the membranes or someone other than the entity performing any or all of the other steps. What is important is that the characteristics of the membrane relative to the analysis to be performed and information desired are well understood. Next, in step 210, the fluid sample is prepared. This preparation step may be as simple as obtaining an existing fluid sample from a subject, or as described above, may comprise a dissolution step in which one component of the eventual sample to be analyzed is dissolved in another component, or a step in which non-soluble particles are suspended in a slurry or other mixture, or the like.

Next, the fluid sample is optionally separated into one or more fractions, in step 220. The separation step may comprise a pre-filtration step to remove components having a size above a certain particle threshold, or a magnetic separation step to separate magnetic or non-magnetic particles, or any other step that physically, chemically, or otherwise separates one fraction of the sample from another. It should be noted that each of the separated fractions may be subjected to the remaining steps, or one of the separated fractions may be discarded, retained for later analysis, or analyzed using a different methodology.

In step 230, at least one fraction of the fluid sample is subjected to the one or more membranes. By "subjected," it is meant that the fluid sample is either passed through the membrane or contacts the membrane for a sufficient time to produce a desired degree of diffusion into the membrane. Regardless of the mechanism for retention, in step 240 one or more components of the liquid sample are retained in or on the one or more membranes. It should be noted here that in the example of membranes with different pore sizes, the sample may first contact a first membrane with a relatively larger pore size such that the retained components comprise particles having a first range of particle sizes greater than or equal to the membrane pore size, and the sample may next contact a second membrane with a relatively smaller pore size than the first membrane, to capture particles having a range of particle sizes between the pore sizes of the first and second membranes. Thus, a single fluid sample may be captured on or in one or more (possibly hundreds) of pre-characterized membranes in which each membrane retains some but not all components of the sample, including but not limited to large bio-macromolecules, bacteria, compounds, ions, magnetized particles, etc.

Next, in step 250, the components retained in or on one or more of the membranes may optionally be fixed to the subject membrane(s), such as by solidifying or otherwise drying the sample, as described herein above. Whether some or all of membranes benefit from such a fixation step may be dependent upon the characteristics of the membrane and the sample fraction retained thereon.

Finally, in step 260, the one or more membranes are analyzed. Although described herein primarily as a sample preparation method for LIBS analysis, the invention is not limited to any particular type of analysis. For methods including LIBS analysis, the LIBS measurements are performed on each membrane separately to acquire a LIBS spectrum for each. The acquired LIBS spectrum may then be analyzed with multi-variate analysis methods, including but not limited to principal component analysis (PCA) as well as any automatic machine learning techniques for feature selection, such as for example: techniques using support vector machines, neural networks, adaptive local hyperplane, K-nearest neighbors, soft independent modeling class analysis, partial least square, and others.

The membranes used to carry out the methods disclosed herein are preferably well defined and well characterized, and in particular, their LIBS spectrum is well and accurately recorded. Exemplary suitable membranes include but are not limited to hydrophilic glass filters in a variety of pore sizes. Filters with larger pore diameters may be used for pre-filtering. For example, a 0.7 µm pore size glass fiber filters may be a suitable pre-filter when used in combination with 0.9 to 8 µm filters for proteinaceious and heavily contaminated liquids.

The methods disclosed herein may be particularly useful when it is desired to analyze and characterize all of the components of a fluid sample. In certain embodiments, it may also be desirable to optionally trap and capture gases given off of the sample during the fixation/drying step and to analyze the gaseous fraction independently, such as by using LIBS analysis, as shown in step 270 of FIG. 2. In some embodiments, if desired, particulates captured on a membrane can be washed via a washing step, provided the wash solution is also known and well-characterized by LIBS.

Although discussed herein primarily with respect to embodiments in which the membranes are porous, the methods as described herein may also be applicable to membranes that are not porous, such as membranes that have a diffusivity for various constituents of the sample into the membrane. Thus, a membrane having known diffusivity characteristics for one or more potential constituents in the sample may be contacted with the sample for a requisite amount of time to promote an expected degree of diffusion, and the LIBS analysis can be performed at different depths (or if the membrane is contacted only in a particular location, at different distances) from the location in which the sample contacts the membrane, for detection of constituents based upon an expected degree of diffusivity for the amount of time the membrane or portion of the membrane was in contact with the liquid. Thus, rather than a method in which the sample is passed through one or more membranes, the method may comprise contacting the sample with one or more membranes or portions thereof, in which at least one characteristic different among the one or more membranes may be a degree of diffusivity relative to a certain potential component, components, or class of components of interest in the sample.

The processes described herein may be assisted by externally enhancing diffusivity or porosity through the membrane, such as but not limited to, by creating a differential pressure (e.g. via positive pressure created by a pump on inlet side of the membrane and/or negative pressure created by a source of vacuum on the outlet side of the membrane) and/or a combination of electromagnetic fields to direct charged particles in the fluid to specific areas of the membrane. Once the process reaches a stable state, the external enhancements (differential pressure and/or electromagnetic fields) are removed and the LIBS analysis can proceed.

The processes described herein generally provide certain advantages for making LIBS measurements on liquids relative to previously known methods. In particular, the multi-membrane processes described herein permit a user to obtain separate analysis for portions of a sample that are size specific (tailored to the size of the constituents of the sample). Depending on the interest of the user, certain users may search for ions, magnetized particles, large or small bio-macromolecules, bacteria, etc.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A method for analyzing a fluid sample containing one or more soluble or insoluble components, the method comprising the steps of:
   (a) providing a plurality of membranes, each membrane having one or more known characteristics in an absence of the one or more soluble or insoluble components, including at least a known LIBS spectra, at least one first membrane having at least one characteristic different from at least one second membrane;
   (b) filtering or diffusing the fluid sample through or into the plurality of membranes;
   (c) retaining one or more components of the fluid sample on or in each of the plurality of membranes and
   (d) analyzing each of the plurality of membranes in the presence of the retained one or components of the fluid sample using laser induced breakdown spectroscopy (LIBS) to obtain a LIBS spectrum for each membrane in the presence of the retained one or more components, and
   (e) reporting (i) a LIBS analysis corresponding to each membrane in the presence of the retained one or more components, along with (ii) information regarding one or more of the known characteristics of each membrane.

2. The method of claim 1, wherein the fluid sample comprises a liquid, a solution, a melt or a slurry.

3. The method of claim 1, wherein the soluble or insoluble components comprise elemental, molecular or biological components.

4. The method of claim 1, wherein at least one of the plurality of membranes is non-magnetic or weakly magnetic.

5. The method of claim 1, wherein the characteristic is selected from the group consisting of: porosity, pore size, pore shape, materials of construction, and a combination thereof.

6. The method of claim 1, wherein each of the plurality of membranes has a pore size between 10 nm and 10 mm.

7. The method of claim 1, wherein at least one of the plurality of membranes is not chemically reactive with the fluid sample.

8. The method of claim 7, wherein at least one of the plurality of membranes is a glass filter.

9. The method of claim 1, wherein step (c) comprises quantifying atomic elements present in the components retained by each of the one or more membranes using LIBS.

10. The method of claim 9, wherein the information regarding the one or more known characteristics of each membrane includes information relating to a particle size or range of particle sizes of the components retained by each membrane.

11. The method of claim 9, further comprising classifying the components retained by each membrane by analyzing the LIBS spectrum using a multi-variate analysis method.

12. The method of claim 11, wherein the multi-variate analysis method comprises a principal component analysis (PCA) method.

13. The method of claim 11, wherein the multi-variate analysis method comprises an automatic machine learning technique selected from the group consisting of: support vector machine techniques, neural networks techniques, adaptive local hyperplane techniques, K-nearest neighbors techniques, soft independent modeling class analysis techniques, and partial least square techniques.

14. The method of claim 1, further comprising the step of characterizing the plurality of membranes prior to performing step (a), wherein the characterizing comprises acquiring a LIBS spectra for the one or more membranes.

15. The method of claim 14, wherein the characterizing further comprises characterizing the one or more membranes with respect to pore size, pore shape, and elemental composition.

16. The method of claim 1, further comprising preparing the sample prior to step (a) by conducting a dissolution step or a separation step.

17. The method of claim 1, comprising diffusing the fluid sample through at least one membrane of the one or more membranes by contacting the at least one membrane with the sample in a sample-membrane-contact location for a requisite amount of time to promote a degree of diffusion, and analyzing the components retained on the membrane using LIBS analysis performed at different distances from the sample-membrane contact location.

18. The method of claim 17, wherein the sample-membrane-contact location comprises a surface of the membrane and the different distances comprise different depths along a thickness of the membrane.

19. The method of claim 17, wherein the sample-membrane-contact location comprises a spot on a surface of the membrane and the different distances comprise different radial distances from the spot along the surface of the membrane.

20. The method of claim 17, wherein the one or more membranes comprises a plurality of membranes in which at least one first membrane has at least one characteristic different from at least one second membrane, wherein the at least one characteristic different comprises a degree of diffusivity relative to one or more components or classes of components of interest for analysis in the sample.

21. A method for analyzing a fluid sample containing one or more insoluble components, the method comprising the steps of:
   (a) providing one or more membranes each membrane having one or more known characteristics, including at least a known LIBS spectra in the absence of the one or more soluble or insoluble components wherein at least one of the one or more membranes is a hydrophilic glass filter;
   (t) filtering or diffusing the fluid sample through or into the one or more membranes and retaining one or more components of the fluid sample on or in each of the one or more membranes;
   (c) analyzing each of the plurality of membranes using laser induced breakdown spectroscopy (LIBS) to obtain a LIDS spectrum for each membrane in the presence of the retained one or more components, and reporting (i) a LIBS analysis corresponding to each membrane in the presence of the retained one or more components, along with (ii) information regarding one or more of the known characteristics of each membrane.

22. The method of claim 21, wherein the one or more membranes comprises a plurality of membranes in which at least one first membrane has at least one characteristic different from at least one second membrane.

23. A method for analyzing a fluid sample containing one or more soluble or insoluble components, the method comprising the steps of:
  (a) providing one or more membranes, each membrane having one or more known characteristics in an absence of the one or more soluble or insoluble components, including at least a known LIBS spectra;
  (b) filtering or diffusing the fluid sample through or into the one or more membranes and retaining one or more components of the fluid sample on or in each of the one or more membranes;
  (c) fixing one or more of the retained components in or on the one or more membranes;
  (d) analyzing each of the one or more membranes in the presence of the retained one or more components of the fluid sample using laser induced breakdown spectroscopy (LIBS) to obtain a LIBS spectrum for each membrane in the presence of the retained one or more components, and
  (e) reporting (i) a LIBS analysis corresponding to each membrane in the presence of the retained one or more components along with (ii) information regarding one or more of the known characteristics of each membrane.

24. The method of claim 23, wherein the fixing step comprises solidifying one or more of the retained components.

25. The method of claim 23, wherein the fixing step comprises removing moisture and hydrates from one or more of the retained components.

26. The method of claim 23, wherein the fixing step comprises subjecting the membrane with the retained components to a method selected from the group consisting of:
  (i) using air convection to remove moisture,
  (ii) using a thermo electric cooler or a thermo electric heater,
  (iii) fixing the liquid on the membranes using radiation; and
  (iv) a combination of any of (i)-(iii).

27. The method of claim 23, further comprising trapping and capturing any gases given off by retained components sample during the fixation step and independently analyzing the gaseous fraction.

28. A method for analyzing a fluid sample containing one or more soluble or insoluble components, the method comprising the steps of:
  (a) magnetizing the sample;
  (b) magnetically physically separating the sample into a portion containing magnetic particles and a portion containing non-magnetic particles;
  (c) providing one or more membranes, each membrane having one or more known characteristics in an absence of the one or more soluble or insoluble components including at least a known LIBS spectra;
  (d) filtering or diffusing a portion of the fluid sample through or into the one or more membranes and retaining one or more components of the fluid sample on or in each of the one or more membrane;
  (e) analyzing each of the one or more membranes in the presence of the retained one or more components of the fluid sample using laser induced breakdown spectroscopy (LIBS) to obtain a LIBS spectrum for each membrane with the retained one or more components, and
  (f) reporting (i) a LIBS analysis corresponding to each membrane in the presence of the retained one or more components, along with (ii) information regarding one or more of the known characteristics of each membrane.

29. The method of claim 28, further comprising using the portion containing magnetic particles as the fluid sample in step (d).

30. The method of claim 28, further comprising using the portion containing the non-magnetic particles as the fluid sample in step (d).

31. The method of claim 28, further comprising separately performing step (d), step (e), or both steps (d) and (e) on both the portion containing magnetic particles and the portion containing the non-magnetic particles.

* * * * *